US009885685B2

(12) United States Patent
Surnilla et al.

(10) Patent No.: US 9,885,685 B2
(45) Date of Patent: Feb. 6, 2018

(54) COMPENSATING OXYGEN SENSOR AGING (71) Applicant: Ford Global Technologies, LLC, Dearborn, MI (US)

(72) Inventors: Gopichandra Surnilla, West Bloomfield, MI (US); Richard E. Soltis, Saline, MI (US); Daniel A. Makled, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 582 days.

(21) Appl. No.: 14/512,342

(22) Filed: Oct. 10, 2014

(65) Prior Publication Data

US 2016/0103095 A1 Apr. 14, 2016

(51) Int. Cl.
*G01N 27/407* (2006.01)
*G01N 27/41* (2006.01)
*G01N 27/406* (2006.01)
*F02D 41/14* (2006.01)

(52) U.S. Cl.
CPC ......... *G01N 27/41* (2013.01); *F02D 41/1456* (2013.01); *F02D 41/1494* (2013.01); *G01N 27/4067* (2013.01)

(58) Field of Classification Search
CPC ........................................ G01N 27/406–27/41
USPC ..................... 204/424–429; 73/23.31–23.32; 123/672–704
See application file for complete search history.

(56) References Cited

U.S. PATENT DOCUMENTS

| | | | |
|---|---|---|---|
| 4,178,793 A | 12/1979 | Bremer et al. | |
| 5,245,979 A | 9/1993 | Pursifull et al. | |
| 5,973,542 A | 10/1999 | Okayasu et al. | |
| 6,258,232 B1 * | 7/2001 | Hasegawa | G01N 27/4067 204/424 |
| 6,371,097 B1 | 4/2002 | Rossi | |
| 6,468,478 B1 | 10/2002 | Honda | |
| 7,197,866 B2 | 4/2007 | Cook et al. | |
| 7,861,515 B2 | 1/2011 | Brahma | |
| 8,296,042 B2 | 10/2012 | Xiao et al. | |
| 8,495,996 B2 | 7/2013 | Soltis et al. | |
| 8,522,760 B2 | 9/2013 | Soltis | |
| 8,603,310 B2 * | 12/2013 | Ishida | G01N 27/419 123/703 |
| 8,763,594 B2 | 7/2014 | Surnilla et al. | |
| 8,857,155 B2 | 10/2014 | Surnilla et al. | |
| 2002/0112605 A1 | 8/2002 | Motouji et al. | |
| 2002/0179594 A1 * | 12/2002 | Hada | G01N 27/4067 219/494 |

(Continued)

OTHER PUBLICATIONS

Surnilla, Gopichandra et al., "Methods and Systems for Fuel Ethanol Content Determination Via an Oxygen Sensor," U.S. Appl. No. 14/151,574, filed Jan. 9, 2014, 31 pages.

(Continued)

*Primary Examiner* — Bach T Dinh
(74) *Attorney, Agent, or Firm* — Julia Voutyras; McCoy Russell LLP (57) ABSTRACT

Various methods are provided for compensating changes in the relation between impedance setpoint and operating temperature in an oxygen sensor. In one embodiment, a method of operating an oxygen sensor comprises adjusting an impedance setpoint based on a change in dry air pumping current of the oxygen sensor.

18 Claims, 5 Drawing Sheets (56) References Cited

U.S. PATENT DOCUMENTS

| | | | |
|---|---|---|---|
| 2008/0189008 A1* | 8/2008 | Iwazaki | F02D 41/1454 |
| | | | 701/114 |
| 2010/0000984 A1 | 1/2010 | Aoki et al. | |
| 2010/0313863 A1* | 12/2010 | Yoshikawa | F02M 35/10222 |
| | | | 123/704 |
| 2013/0133399 A1 | 5/2013 | Hibino | |
| 2014/0202426 A1 | 7/2014 | Surnilla et al. | |
| 2014/0202437 A1 | 7/2014 | Surnilla et al. | |

OTHER PUBLICATIONS

Surnilla, Gopichandra et al., "Methods and Systems for Fuel Ethanol Content Determination Via an Oxygen Sensor," U.S. Appl. No. 14/297,301, filed Jun. 5, 2014, 35 pages.

* cited by examiner

COMPENSATING OXYGEN SENSOR AGING

FIELD

The field of the disclosure generally relates to oxygen sensors.

BACKGROUND AND SUMMARY

Intake and/or exhaust gas sensors may be operated to provide indications of various exhaust gas constituents. Output from an oxygen sensor, for example, may be used to determine the air-fuel ratio (AFR) of exhaust gas. Similarly, an oxygen sensor may be disposed in an engine intake passage to determine the AFR of intake gas. In both cases, indications of intake and exhaust gas AFR may be used to adjust various engine operating parameters such as fueling and a target AFR, for example. In particular, exhaust gas AFR may be controlled to achieve the target AFR in order to maximize operating efficiency of an emission control device. For some oxygen sensors, their output may significantly vary as a function of their operating temperature. As such, these oxygen sensors may be heated by a heating element to achieve a desired operating temperature range such that desired oxygen sensing is provided.

The inventors herein have recognized that aging in an oxygen sensor such as a universal exhaust gas oxygen (UEGO) sensor can change the relation between temperature and impedance. For example, an impedance that results in a desired sensor temperature in a non-aged UEGO sensor may differ from an impedance that results in the desired sensor temperature in an aged UEGO. Without compensating this change in the relation between sensor temperature and impedance, the heater of the aged UEGO may be controlled to achieve the impedance that would achieve the desired sensor temperature in the non-aged UEGO sensor. Instead, an undesired sensor temperature which overshoots the desired sensor temperature may result, which may cause inaccurate sensor output and thus degraded engine operation.

U.S. Pat. No. 4,178,793 discloses an apparatus for measuring the impedance of an exhaust gas oxygen sensor. In one example, an oxygen sensor includes a variable internal impedance and is connected in series with a reference impedance and a semiconductor switch. A constant current source supplies current to a junction of the sensor and reference impedance at one sensor terminal to provide a minimum current and small switch impedance when the sensor impedance is large. The magnitude of the voltage at the one sensor terminal with the semiconductor switch in its conducting and non-conducting states may be sampled. The ratio of the magnitudes varies with sensor impedance. The ratio may be compared with one or more references to, in some examples, control operation of a sensor heater. In some scenarios, the comparison may prompt heating of the sensor via the heater to achieve a desired sensor impedance.

The inventors herein have recognized several issues with the approach identified above. While provision of dedicated sensor impedance sensing circuitry may facilitate sensor impedance measurement over time, inclusion of the circuitry increases the cost, complexity, and packaging space associated with the sensor arrangement. Moreover, other factors that can affect oxygen sensing are not accounted for—e.g., humidity. Inaccurate oxygen sensing may nevertheless result despite the ability to measure oxygen sensor impedance.

One approach that at least partially addresses the above issues includes a method of operating an oxygen sensor, comprising adjusting an impedance setpoint based on a change in dry air pumping current of the oxygen sensor In a more specific example, a heating element coupled to the oxygen sensor is adjusted responsive to the adjusted impedance setpoint.

In a more particular example, the impedance setpoint is adjusted based on a desired operating temperature of the oxygen sensor.

In another aspect of the example, an operating temperature of the oxygen sensor is a function of the adjusted impedance setpoint.

In yet another aspect of the example, the oxygen sensor is a universal exhaust gas oxygen sensor.

In this way, changes in a relation between impedance setpoint of an oxygen sensor and a resulting operating temperature may be compensated. Thus, the technical result is achieved by these actions.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Oxygen sensors are frequently used in internal combustion engines to provide indications of various constituents in gasses. An oxygen sensor may be positioned in an exhaust system of an engine and configured to indicate the air-fuel ratio (AFR) of exhaust gas, for example. Alternatively or additionally, an oxygen sensor may be positioned in an intake system of the engine and configured to indicate the AFR of intake gas. Output from an oxygen sensor may be used to adjust various engine operating parameters, including but not limited to fueling and a target AFR. For some oxygen sensors, their output is highly variable with respect to their operating temperature. As such, a heating element may be used to accurately control the operating temperature of an oxygen sensor.

In some approaches, the impedance of an oxygen sensor may be monitored and used to control the operating temperature of the oxygen sensor, as the impedance and resulting operating temperature correlate highly with each other. Accordingly, a desired operating temperature that provides desired sensor operation may be selected and achieved by controlling the sensor impedance to a desired setpoint. Sensor aging, however, may alter the relation between operating temperature and impedance setpoint such that an impedance setpoint that results in the desired operating temperature in a non-aged oxygen sensor results in an undesired operating temperature in an aged oxygen sensor. Other factors may affect oxygen sensor operation as well, such as humidity.

Figure 1:
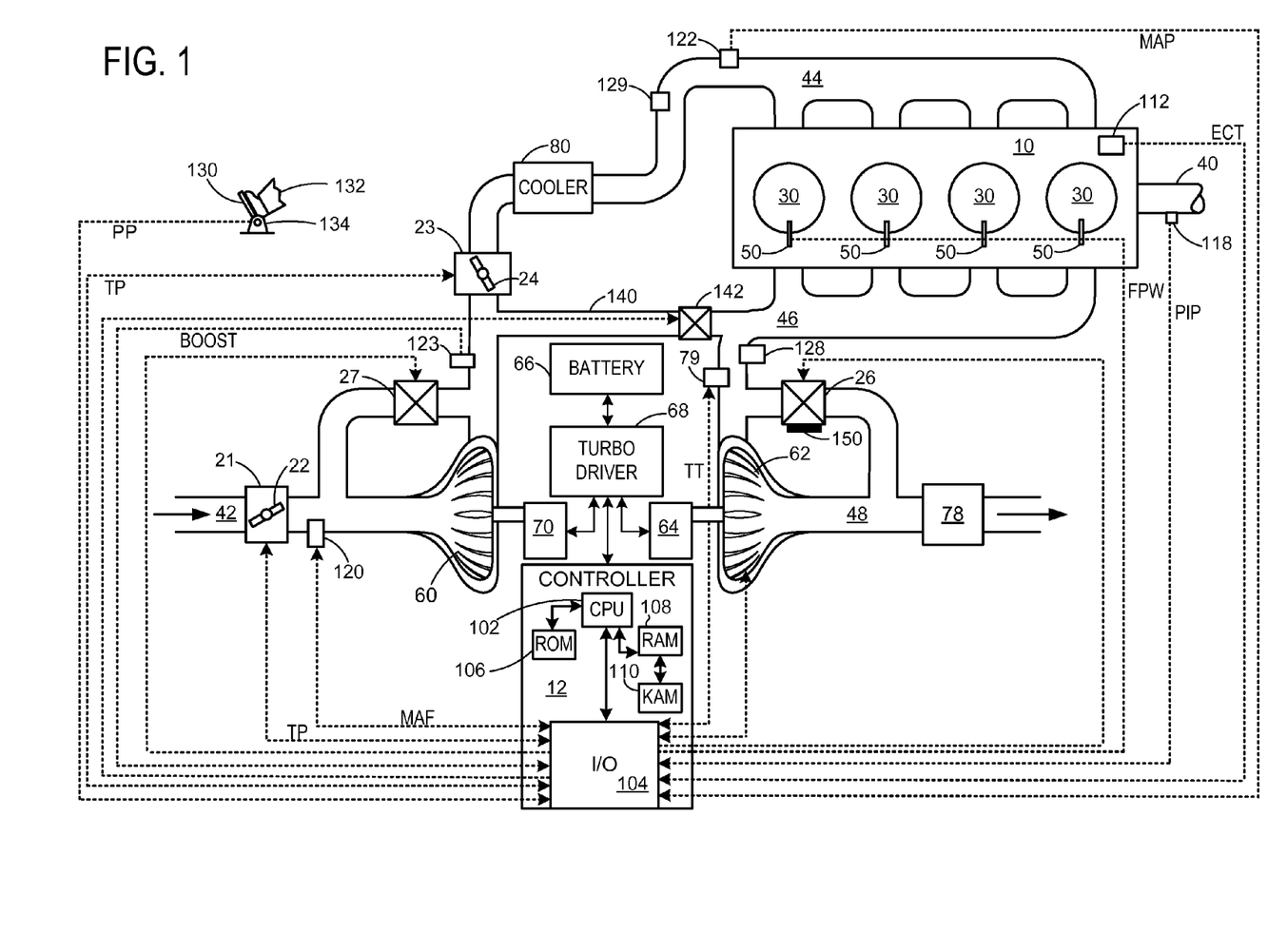
FIG. 1 shows a block diagram of a turbocharged engine.
Figure 2:
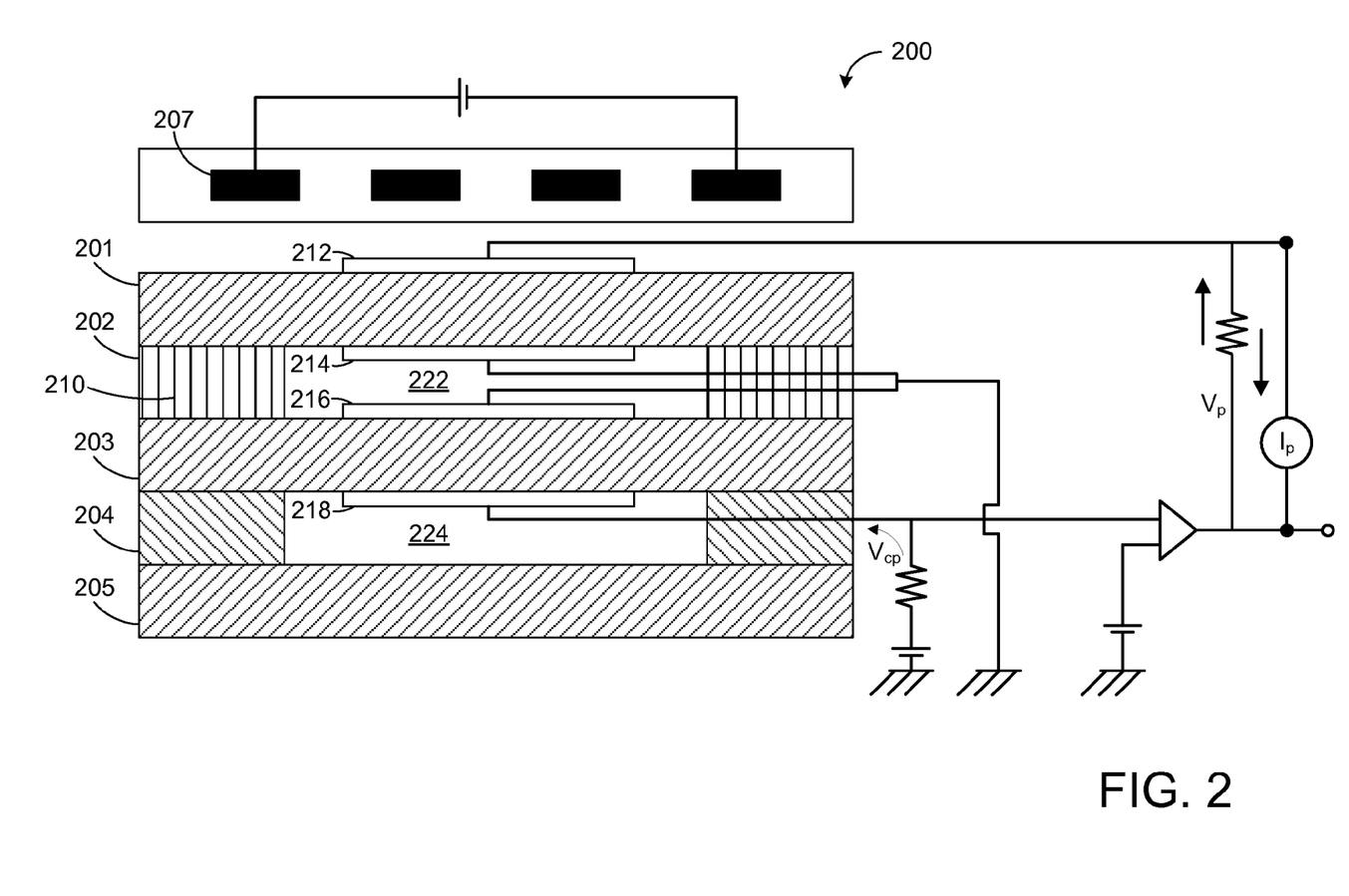
FIG. 2 shows a schematic diagram of an example oxygen sensor.
Figure 3:
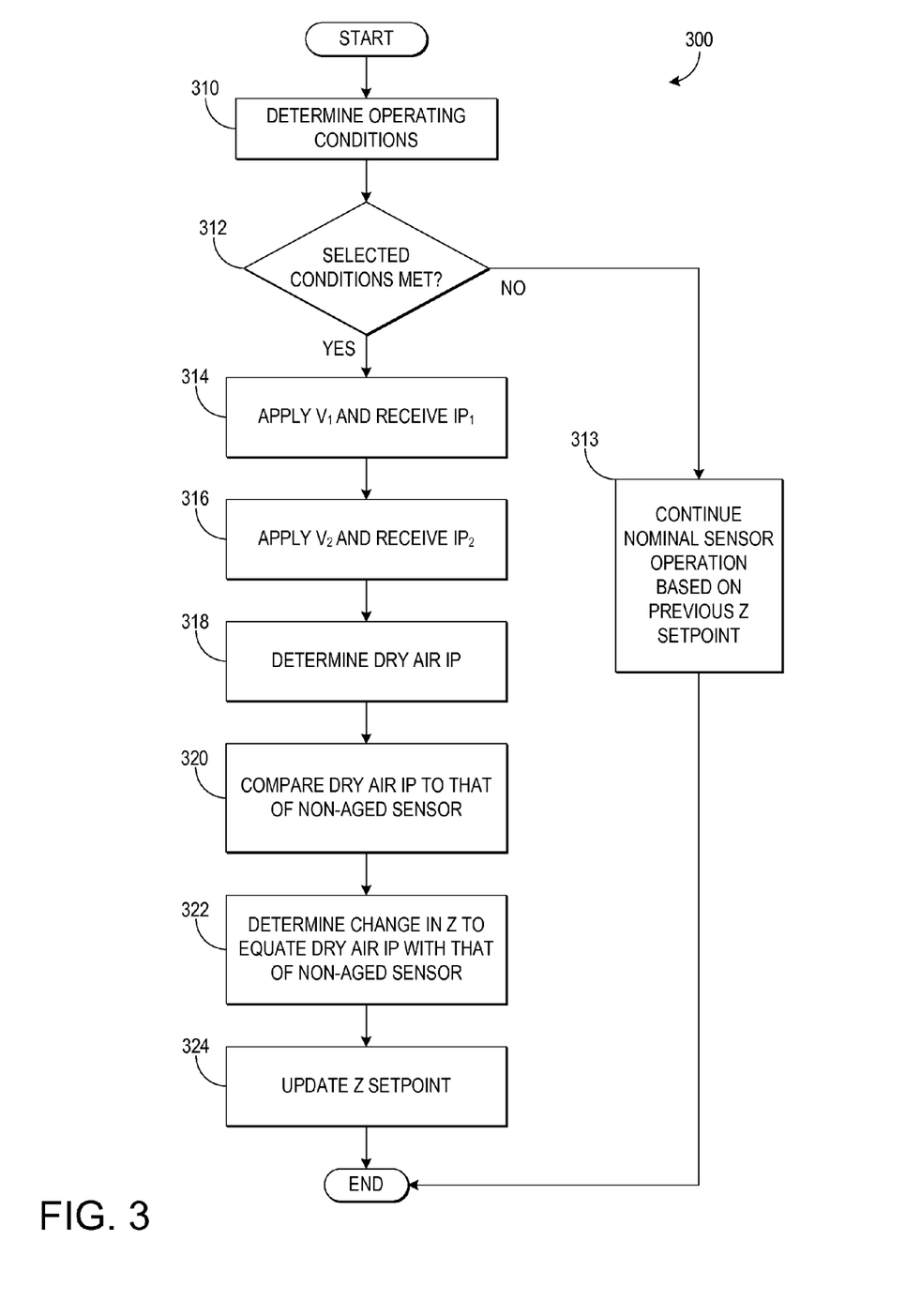
FIG. 3 shows a flowchart illustrating a routine for compensating changes to the relation between impedance and temperature in an oxygen sensor.
Figure 4:
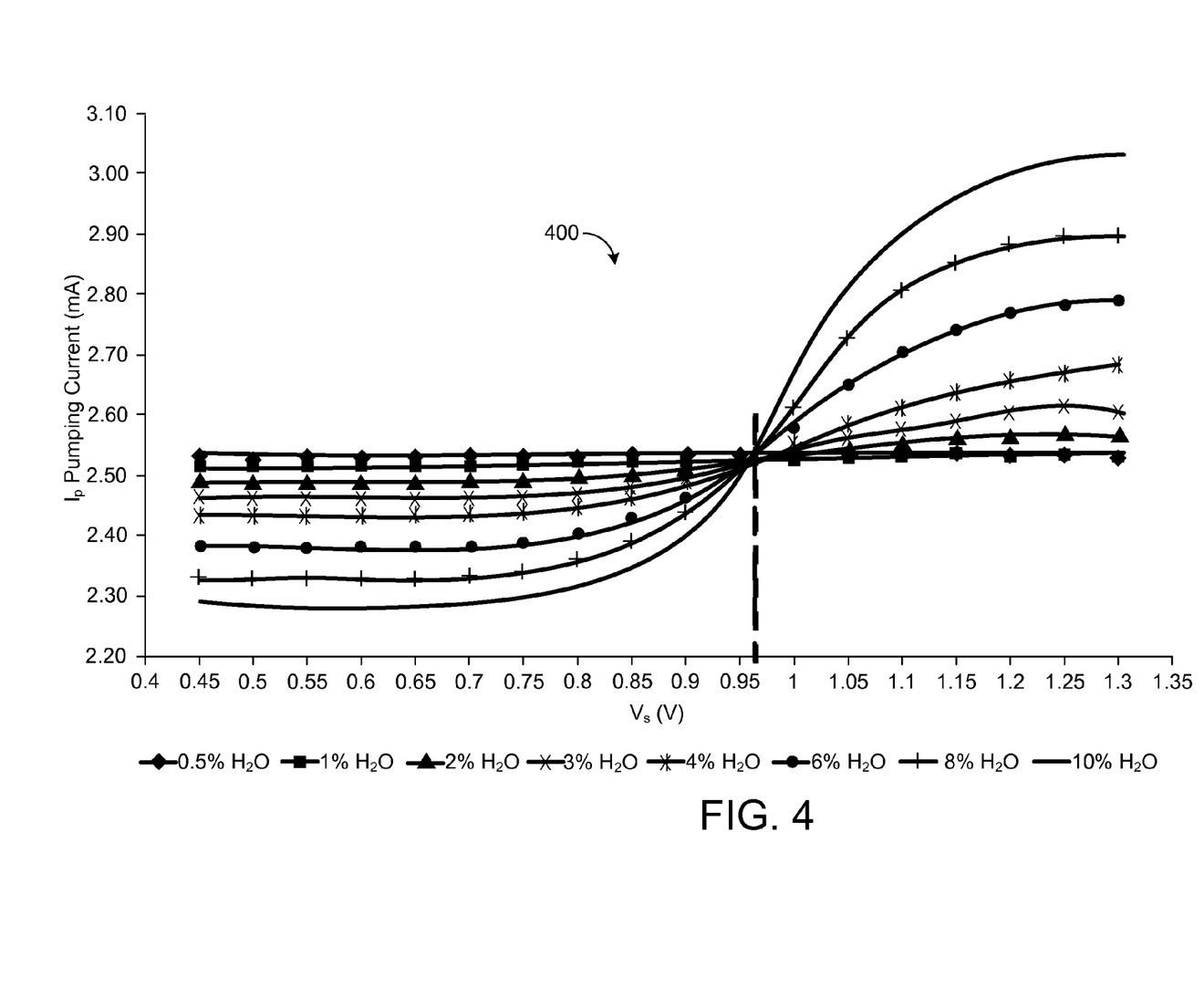
FIG. 4 shows a graph depicting oxygen sensor output under various humidity conditions with respect to applied voltage.
Figure 5:
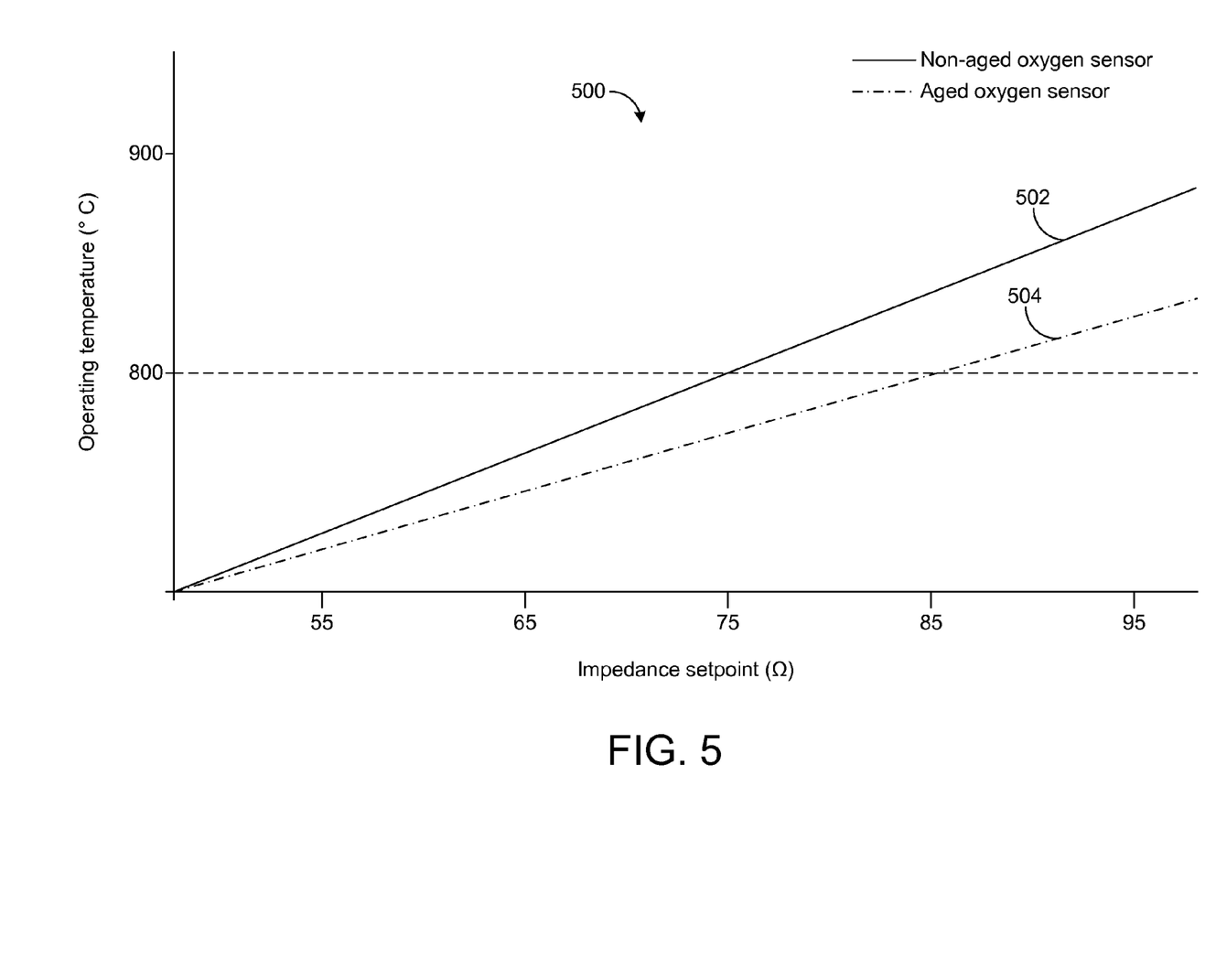
FIG. 5 shows a plot of operating temperature as a function of impedance setpoint for an example oxygen sensor.

Various methods are provided for compensating changes in the relation between impedance setpoint and operating temperature in an oxygen sensor. In one embodiment, a method of operating an oxygen sensor comprises adjusting an impedance setpoint based on a change in dry air pumping current of the oxygen sensor. FIG. 1 shows a block diagram of a turbocharged engine, FIG. 2 shows a schematic diagram of an example oxygen sensor, FIG. 3 shows a flowchart illustrating a routine for compensating changes to the relation between impedance and temperature in an oxygen sensor, FIG. 4 shows a graph depicting oxygen sensor output under various humidity conditions with respect to applied voltage, and FIG. 5 shows a plot of operating temperature as a function of impedance setpoint for an example oxygen sensor. The engine of FIG. 1 also includes a controller to controller configured to carry out the methods depicted in FIG. 3.

FIG. 1 is a schematic diagram showing an example engine 10, which may be included in a propulsion system of an automobile. The engine 10 is shown with four cylinders 30. However, other numbers of cylinders may be used in accordance with the current disclosure. Engine 10 may be controlled at least partially by a control system including controller 12, and by input from a vehicle operator 132 via an input device 130. In this example, input device 130 includes an accelerator pedal and a pedal position sensor 134 for generating a proportional pedal position signal PP. Each combustion chamber (e.g., cylinder) 30 of engine 10 may include combustion chamber walls with a piston (not shown) positioned therein. The pistons may be coupled to a crankshaft 40 so that reciprocating motion of the piston is translated into rotational motion of the crankshaft. Crankshaft 40 may be coupled to at least one drive wheel of a vehicle via an intermediate transmission system (not shown). Further, a starter motor may be coupled to crankshaft 40 via a flywheel to enable a starting operation of engine 10.

Combustion chambers 30 may receive intake air from intake manifold 44 via intake passage 42 and may exhaust combustion gasses via exhaust passage 48. Intake manifold 44 and exhaust manifold 46 can selectively communicate with combustion chamber 30 via respective intake valves and exhaust valves (not shown). In some embodiments, combustion chamber 30 may include two or more intake valves and/or two or more exhaust valves.

Fuel injectors 50 are shown coupled directly to combustion chamber 30 for injecting fuel directly therein in proportion to the pulse width of signal FPW received from controller 12. In this manner, fuel injector 50 provides what is known as direct injection of fuel into combustion chamber 30. The fuel injector may be mounted in the side of the combustion chamber or in the top of the combustion chamber, for example. Fuel may be delivered to fuel injector 50 by a fuel system (not shown) including a fuel tank, a fuel pump, and a fuel rail. In some embodiments, combustion chambers 30 may alternatively, or additionally, include a fuel injector arranged in intake manifold 44 in a configuration that provides what is known as port injection of fuel into the intake port upstream from each combustion chamber 30.

Intake passage 42 may include throttle 21 and 23 having throttle plates 22 and 24, respectively. In this particular example, the position of throttle plates 22 and 24 may be varied by controller 12 via signals provided to an actuator included with throttles 21 and 23. In one example, the actuators may be electric actuators (e.g., electric motors), a configuration that is commonly referred to as electronic throttle control (ETC). In this manner, throttles 21 and 23 may be operated to vary the intake air provided to combustion chamber 30 among other engine cylinders. The position of throttle plates 22 and 24 may be provided to controller 12 by throttle position signal TP. Intake passage 42 may further include a mass air flow sensor 120, a manifold air pressure sensor 122, and a throttle inlet pressure sensor 123 for providing respective signals MAF (mass airflow) MAP (manifold air pressure) to controller 12.

Exhaust passage 48 may receive exhaust gasses from cylinders 30. Exhaust gas sensor 128 is shown coupled to exhaust passage 48 upstream of turbine 62 and emission control device 78. Sensor 128 may be selected from among various suitable sensors for providing an indication of exhaust gas air/fuel ratio such as a linear oxygen sensor or UEGO (universal or wide-range exhaust gas oxygen), a two-state oxygen sensor or EGO, a NOx, HC, or CO sensor, for example. Emission control device 78 may be a three way catalyst (TWC), NOx trap, various other emission control devices, or combinations thereof.

FIG. 1 also illustrates the inclusion of an intake air sensor 129 coupled to intake passage 42. Sensor 129 may be any suitable sensor for providing an indication of intake gas AFR such as a linear oxygen sensor or UEGO (universal or wide-range exhaust gas oxygen), a two-state oxygen sensor or EGO, a HEGO (heated EGO), a $NO_x$, HC, or CO sensor, for example. In some implementations, both sensor 128 and sensor 129 may be included in engine 10 as shown in FIG. 1, while in other implementations one and not the other of sensors 128 and 129 may be included.

Exhaust temperature may be measured by one or more temperature sensors (not shown) located in exhaust passage 48. Alternatively, exhaust temperature may be inferred based on engine operating conditions such as speed, load, AFR, spark retard, etc.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112, shown schematically in one location within the engine 10; a profile ignition pickup signal (PIP) from Hall effect sensor 118 (or other type) coupled to crankshaft 40; the throttle position (TP) from a throttle position sensor, as discussed; and absolute manifold pressure signal, MAP, from sensor 122, as discussed. Engine speed signal, RPM, may be generated by controller 12 from signal PIP. Manifold pressure signal MAP from a manifold pressure sensor may be used to provide an indication of vacuum, or pressure, in the intake manifold 44. Note that various combinations of the above sensors may be used, such as a MAF sensor without a MAP sensor, or vice versa. During stoichiometric operation, the MAP sensor can give an indication of engine torque. Further, this sensor, along with the detected engine speed, can provide an estimate of charge (including air) inducted into the cylinder. In one example, sensor 118, which is also used as an engine speed sensor, may produce a predetermined number of equally spaced pulses every revolution of the crankshaft 40. In some examples, storage medium read-only memory 106 may be programmed with computer readable data representing instructions executable by processor 102 for performing the methods described below as well as other variants that are anticipated but not specifically listed.

Engine 10 may further include a compression device such as a turbocharger or supercharger including at least a compressor 60 arranged along intake manifold 44. For a turbocharger, compressor 60 may be at least partially driven by a turbine 62, via, for example a shaft, or other coupling arrangement. The turbine 62 may be arranged along exhaust passage 48 and communicate with exhaust gasses flowing therethrough. Various arrangements may be provided to drive the compressor. For a supercharger, compressor 60 may be at least partially driven by the engine and/or an electric machine, and may not include a turbine. Thus, the amount of compression provided to one or more cylinders of the engine via a turbocharger or supercharger may be varied by controller 12. In some cases, the turbine 62 may drive, for example, an electric generator 64, to provide power to a battery 66 via a turbo driver 68. Power from the battery 66 may then be used to drive the compressor 60 via a motor 70. Further, a sensor 123 may be disposed in intake manifold 44 for providing a BOOST signal to controller 12.

Further, exhaust passage 48 may include wastegate 26 for diverting exhaust gas away from turbine 62. In some embodiments, wastegate 26 may be a multi-staged wastegate, such as a two-staged wastegate with a first stage configured to control boost pressure and a second stage configured to increase heat flux to emission control device 78. Wastegate 26 may be operated with an actuator 150, which may be an electric actuator such as an electric motor, for example, though pneumatic actuators are also contemplated. Intake passage 42 may include a compressor bypass valve 27 configured to divert intake air around compressor 60. Wastegate 26 and/or compressor bypass valve 27 may be controlled by controller 12 via actuators (e.g., actuator 150) to be opened when a lower boost pressure is desired, for example.

Intake passage 42 may further include charge air cooler (CAC) 80 (e.g., an intercooler) to decrease the temperature of the turbocharged or supercharged intake gasses. In some embodiments, charge air cooler 80 may be an air to air heat exchanger. In other embodiments, charge air cooler 80 may be an air to liquid heat exchanger.

Further, in the disclosed embodiments, an exhaust gas recirculation (EGR) system may route a desired portion of exhaust gas from exhaust passage 48 to intake passage 42 via EGR passage 140. The amount of EGR provided to intake passage 42 may be varied by controller 12 via EGR valve 142. Further, an EGR sensor (not shown) may be arranged within the EGR passage and may provide an indication of one or more of pressure, temperature, and concentration of the exhaust gas. Alternatively, the EGR may be controlled through a calculated value based on signals from the MAF sensor (upstream), MAP (intake manifold), MAT (manifold gas temperature) and the crank speed sensor. Further, the EGR may be controlled based on an exhaust $O_2$ sensor and/or an intake oxygen sensor (intake manifold). Under some conditions, the EGR system may be used to regulate the temperature of the air and fuel mixture within the combustion chamber. FIG. 1 shows a high pressure EGR system where EGR is routed from upstream of a turbine of a turbocharger to downstream of a compressor of a turbocharger. In other embodiments, the engine may additionally or alternatively include a low pressure EGR system where EGR is routed from downstream of a turbine of a turbocharger to upstream of a compressor of the turbocharger.

FIG. 2 shows a schematic view of an example embodiment of an oxygen sensor 200 configured to measure a concentration of oxygen ($O_2$) in an intake airflow in an intake passage or an exhaust gas stream in an exhaust passage. The sensor 200 may thus correspond to one or both of sensors 128 and 129 of FIG. 1, for example. Further, the sensor 200 may be a UEGO sensor in some embodiments.

As shown in FIG. 2, the sensor 200 comprises a plurality of layers of one or more ceramic materials arranged in a stacked configuration. In the embodiment of FIG. 2, five ceramic layers are depicted as layers 201, 202, 203, 204, and 205. These layers include one or more layers of a solid electrolyte capable of conducting ionic oxygen. Examples of suitable solid electrolytes include, but are not limited to, zirconium oxide-based materials. Further, in some embodiments, a heater 207 may be disposed in thermal communication with the layers to increase the ionic conductivity of the layers. While the depicted oxygen sensor is formed from five ceramic layers, it will be appreciated that the oxygen sensor may include other suitable numbers of ceramic layers.

The layer 202 includes a material or materials creating a diffusion path 210. The diffusion path 210 is configured to introduce gasses into a first internal cavity 222 via diffusion. The diffusion path 210 may be configured to allow one or more components of intake air or exhaust gasses, including but not limited to a desired analyte (e.g., $O_2$), to diffuse into internal cavity 222 at a more limiting rate than the analyte can be pumped in or out by a pumping electrodes pair 212 and 214. In this manner, a stoichiometric level of $O_2$ may be obtained in the first internal cavity 222.

The sensor 200 further includes a second internal cavity 224 within the layer 204 separated from the first internal cavity 222 by the layer 203. The second internal cavity 224 is configured to maintain a constant oxygen partial pressure equivalent to a stoichiometric condition; e.g., an oxygen level present in the second internal cavity 224 is equal to that which the intake air or exhaust gas would have if the air-fuel ratio was stoichiometric. The oxygen concentration in the second internal cavity 224 is held constant by pumping voltage $V_{cp}$. Herein, the second internal cavity 224 may be referred to as a reference cell.

A pair of sensing electrodes 216 and 218 is disposed in communication with the first internal cavity 222 and the reference cell 224. The sensing electrodes pair 216 and 218 detects a concentration gradient that may develop between the first internal cavity 222 and the reference cell 224 due to an oxygen concentration in the intake air or exhaust gas that is higher than or lower than the stoichiometric level. A high oxygen concentration may be caused by a lean intake air or exhaust gas mixture, while a low oxygen concentration may be caused by a rich mixture.

A pair of pumping electrodes 212 and 214 is disposed in communication with the internal cavity 222, and is configured to electrochemically pump a selected gas constituent (e.g., $O_2$) from internal cavity 222 through layer 201 and out of the sensor 200. Alternatively, the pair of pumping electrodes 212 and 214 may be configured to electrochemically pump a selected gas through layer 201 and into internal cavity 222. Herein, the pumping electrodes pair 212 and 214 may be referred to as an $O_2$ pumping cell.

The electrodes 212, 214, 216, and 218 may be made of various suitable materials. In some embodiments, the electrodes 212, 214, 216, and 218 may be at least partially made of a material that catalyzes the dissociation of molecular oxygen. Examples of such materials include, but are not limited to, electrodes containing platinum and/or silver.

The process of electrochemically pumping the oxygen out of or into the internal cavity 222 includes applying a voltage $V_p$ across the pumping electrode pair 212 and 214. The pumping voltage $V_p$ applied to the $O_2$ pumping cell pumps oxygen into or out of the first internal cavity 222 in order to maintain a stoichiometric level of oxygen in the cavity pumping cell. The resulting pumping current $I_p$ is proportional to the concentration of oxygen in the exhaust gas. A suitable control system (not shown in FIG. 2) generates the pumping current signal $I_p$ as a function of the intensity of the applied pumping voltage $V_p$ required to maintain a stoichiometric level within the first internal cavity 222. Thus, a lean mixture will cause oxygen to be pumped out of the internal cavity 222 and a rich mixture will cause oxygen to be pumped into the internal cavity 222.

It should be appreciated that the oxygen sensor described herein is merely an example embodiment of an oxygen sensor, and that other embodiments of oxygen sensors may have additional and/or alternative features and/or designs.

It is well known that the conductivity of a material changes with temperature. For an oxygen ionic conducting electrolyte such as zirconia, the ionic conductivity typically increases as the temperature increases. Other factors such as impurities, grain boundaries, structure, and geometry can affect the conductivity of the zirconia. For a fixed geometry and structure, the impedance (which is the inverse of the conductivity) of a zirconia element is directly related to the temperature of the element. The impedance of the sensor element can be measured by measuring the voltage drop across the sensor element, for example by using an AC technique. For oxygen sensor 200, the impedance may be specifically measured across either the sensing cell that is comprised of layer 203 and electrodes 216 and 218, or the pumping cell that is comprised of layer 201 and electrodes 212 and 214, for example.

A suitable control system (not shown in FIG. 2) may control heater 207 to achieve a desired temperature of oxygen sensor 200. The desired temperature may be selected such that sensor 200 provides desired oxygen sensing. To determine the operating temperature of sensor 200, the control system may measure the impedance of the sensor, based on the pumping voltages $V_{cp}$ and $V_p$, and the pumping current $I_p$, for example. Thus, achieving a desired sensor impedance may be interpreted as an indicator that the desired sensor temperature was achieved. As described above, however, aging in an oxygen sensor may alter a nominal relation between sensor impedance and sensor temperature. Other factors, such as humidity in gasses flowing through sensor 200, may affect oxygen sensing by the sensor. Without compensating these factors, sensor 200 may reach an undesired operating temperature despite achieving a desired impedance. As a nonlimiting example, a UEGO sensor operating nominally (e.g., a non-aged UEGO sensor) may reach 800° C. for an impedance of 75Ω. An aged counterpart UEGO sensor, however, may exhibit a significantly different impedance when operating at 800° C.—e.g., 100Ω. As such, when the impedance of the aged UEGO sensor reaches 75Ω, its temperature may correspond to 900° C., outside of the desired operating temperature. It will be understood that, in some examples, the desired operating temperature may be a range of operating temperatures that may be selected prior to implementation of the sensor based on known properties of the sensor (e.g., material and electrochemical properties).

FIG. 3 shows a flowchart illustrating a routine 300 for compensating changes to the relation between impedance and temperature in an oxygen sensor. Routine 300 may be employed to compensate such changes in sensors 128, 129, and/or 200, for example, and generally such changes in UEGO sensors. In some examples, these changes may be the result of sensor aging.

At 310 of routine 300, engine operating conditions are determined. Engine operating conditions may include but are not limited to AFR, amount of EGR entering the combustion chambers, and fueling conditions, for example.

Once the engine operating conditions are determined, routine 300 continues to 312 where it is determined if selected conditions are met. For example, when the oxygen sensor is an intake oxygen sensor positioned in the intake passage, the selected conditions may include EGR being enabled and no purge or crankcase ventilation gasses being received in the intake manifold. As another example, when the oxygen sensor is an exhaust gas oxygen sensor positioned in the exhaust passage, the selected conditions may include engine non-fueling conditions. Non-fueling conditions include vehicle deceleration conditions and engine operating conditions in which the fuel supply is interrupted but the engine continues spinning and at least one intake valve and one exhaust valve are operating; thus, air is flowing through one or more of the cylinders, but fuel is not injected in the cylinders. Under non-fueling conditions, combustion is not carried out and ambient air may move through the cylinder from the intake to the exhaust. In this way, an oxygen sensor, such as an intake or exhaust oxygen sensor, may receive ambient air on which measurements, such as ambient humidity detection, may be performed.

As noted, non-fueling conditions may include, for example, deceleration fuel shut-off (DFSO). DFSO is responsive to the operator pedal (e.g., in response to a driver tip-out and where the vehicle decelerates greater than a threshold amount). DSFO conditions may occur repeatedly during a drive cycle, and, thus, numerous indications of the ambient humidity may be generated throughout the drive cycle, such as during each DFSO event.

If it is determined that selected operating conditions are not met (NO), routine 300 continues to 313 where nominal operation of the oxygen sensor is continued based on a previous impedance set point. In some examples, nominal sensor operation may include nominal oxygen sensing. The previous impedance set point may be a nominal impedance set point whose application results in a desired operating temperature for a non-aged oxygen sensor. In other examples, however, the previous impedance set point may be a previously determined non-nominal impedance set point determined, stored, and retrieved according to routine 300 as described below.

Continuing with FIG. 3, if is determined that selected operating conditions are met (YES), routine 300 continues to 314 where a first pumping voltage ($V_1$) is applied to the oxygen pumping cell of the exhaust gas sensor and a first pumping current ($I_{p1}$) is received. The first pumping voltage may have a value such that oxygen is pumped from the cell, but low enough that oxygen compounds such as $H_2O$ (e.g., water) are not dissociated (e.g., $V_1$=450 mV). Application of the first voltage generates an output of the sensor in the form of the first pumping current ($I_{p1}$) that is indicative of the amount of oxygen in the sample gas. In this example, because the engine is under selected conditions (such as non-fueling conditions), the amount of oxygen may correspond to the amount of oxygen in the fresh air surrounding the vehicle, or a humid air oxygen reading.

Once the amount of oxygen is determined, routine 300 proceeds to 316 where a second pumping voltage ($V_2$) is applied to the oxygen pumping cell of the sensor and a second pumping ($I_{p2}$) current is received. The second voltage may be greater than the first voltage applied to the sensor. In particular, the second voltage may have a value high enough to dissociate a desired oxygen compound. For example, the second voltage may be high enough to dissociate $H_2O$ molecules into hydrogen and oxygen (e.g., $V_2$=1.1 V). Application of the second voltage generates the second pumping current ($I_{p2}$) that is indicative of the amount of oxygen and water in the sample gas. It will be understood that the term "water" in the "amount of oxygen and water" as used herein refers to the amount of oxygen from the dissociated $H_2O$ molecules in the sample gas.

In one particular example, the second voltage may be 950 mV, at which the water in the air is partially dissociated (e.g., 40% of the water in the air is dissociated at 950 mV). As an example, a graph 400 of FIG. 4 shows oxygen sensor output over a range of humidity conditions (e.g., from 0.5% humidity to 10% humidity). As shown, the sensor output at 950 mV corresponds to a dry air reading under the range of humidity conditions. Thus, a dry air oxygen reading may be obtained when the oxygen sensor is operated at 950 mV. In this way, a dry air pumping current ($I_{pdry}$) of the oxygen sensor may be determined under two different humidity conditions.

At 318, a dry air pumping current ($I_{pdry}$) of the oxygen sensor is determined. The dry air pumping current may be the pumping current received when a corresponding pumping voltage is applied to the oxygen pumping cell of the sensor in dry air, and may be used as a correction to subsequent measurements made by the sensor. In some examples, the dry air pumping current is determined based on the first and second pumping currents ($I_{p1}$ and $I_{p2}$) according to the following relation: $I_{pdy}=(I_{p2}*0.4)+(I_{p1}*0.6)$. Alternative mechanisms of determining the dry air pumping current are possible, however.

At 320, the dry air pumping current of the oxygen sensor is compared to the dry air pumping current of a non-aged (e.g., new) oxygen sensor. The pumping current of the non-aged oxygen sensor may be determined offline in a testing environment and stored in a suitable data structure, for example. In some examples, comparison of these dry air pumping currents may include determining their difference.

At 322, the change in impedance (Z) of the oxygen sensor required to equate the dry air pumping current of the oxygen sensor to the dry air pumping current of the non-aged oxygen sensor (e.g., a nominal dry air pumping current) is determined. In some examples, the impedance change may be determined by multiplying the difference in the dry air pumping currents by a suitable constant that relates pumping current to impedance (e.g., the constant has units of $\Omega$/mA). The constant may be the gain of change in impedance per 1 mA of pumping current, and may be determined offline in a testing environment specific to the oxygen sensor, for example.

At 324, an impedance setpoint of the oxygen sensor is adjusted. The impedance setpoint may be adjusted by adding the change in impedance determined at 322 to the impedance setpoint, for example. In some embodiments, a suitable data structure (e.g., lookup table) that stores one or more impedance setpoints and one or more resulting operating temperatures may be updated responsive to adjustment of the impedance setpoint. In some examples, adjustment of the impedance setpoint may prompt adjustment of a function that outputs impedance setpoints as a function of desired operating temperature.

In some embodiments, the dry air pumping current of the oxygen sensor may be returned from the value determined at 318 to a nominal value (e.g., 4.0 mA) corresponding to the dry air pumping current associated with a non-aged oxygen sensor, following adjustment of the impedance setpoint. By bringing the dry air pumping current of an aged sensor to the nominal value, the calibration of a nominal sensor may be used at all times. This may modify the behavior of sensors with large part to part variability and sensors that change to a great extent with aging such that the modified behavior corresponds to that of a new sensor with a nominal transfer function. Also, by modifying an aged sensor to match its behavior to that of a nominal sensor, any actions taken (e.g., adding a compensating resistor, sorting sensors based on output) to reduce part to part variability can be eliminated, resulting in reduced sensor cost. Generally, returning the dry air pumping current value to the nominal value may enable mitigation of aging and/or other degrading effects on a sensor.

As described above, the impedance setpoint may be a parameter selected to achieve a desired oxygen sensor operating temperature at which desired sensor operation may be achieved. Since aging in the oxygen sensor may change the relation between impedance setpoint and resulting operating temperature, adjustment of the impedance setpoint according to routine 300 may facilitate achievement of desired oxygen sensor operating temperatures that have undergone aging. In this way, the useful life of an oxygen sensor may be increased. Moreover, high operating temperatures that can potentially degrade operation of an oxygen sensor may be avoided by adjusting the impedance setpoint as described herein, whereas in other approaches the oxygen sensor may be controlled to reach unacceptably high operating temperatures as a natural consequence of sensor aging, as unadjusted impedance setpoints increasingly map to relatively higher operating temperatures.

As such, operation of an oxygen sensor according to the approaches described herein may include accessing a data structure to retrieve adjusted impedance setpoints so that desired operating temperatures are achieved. A heating element (e.g., heater 207 of FIG. 2) coupled to the oxygen sensor may then be adjusted according to adjusted impedance setpoints. Adjusting the heating element in this way may include measuring the impedance of the oxygen sensor, for example in a closed-loop control arrangement in which the heating element is controlled to achieve a desired impedance setpoint with the instant measured impedance being fed back to heating element controls.

A nonlimiting example of impedance setpoint adjustment in an oxygen sensor follows. In this example, the dry air pumping current of a non-aged oxygen sensor is 4.0 mA and its impedance setpoint is 75$\Omega$. As this oxygen sensor has not undergone significant aging, a desired operating temperature (e.g., 800° C.) may be achieved by controlling the sensor based on the impedance setpoint of 75$\Omega$. In contrast, the dry air pumping current of an aged oxygen sensor is determined to be 4.2 mA. This change in dry air pumping current may be the result of increased operating temperature of the aged oxygen sensor when controlled to the unadjusted impedance setpoint of 75$\Omega$, for example. Thus, the difference between the aged and non-aged pumping currents is 0.2 mA. This pumping current difference is then multiplied by a constant (e.g., 50$\Omega$/mA) to yield an impedance setpoint adjustment of 10Ω. Accordingly, the impedance setpoint of the aged oxygen sensor is adjusted—e.g., by adding the non-adjusted impedance setpoint to the impedance setpoint adjustment, yielding an adjusted impedance setpoint of 85Ω. Now, controlling the aged oxygen sensor according to the adjusted impedance setpoint of 85Ω may bring the oxygen sensor to the desired operating temperature (e.g., 800° C.), whereas controlling the oxygen sensor based on the unadjusted impedance setpoint of 75Ω would result in an undesired operating temperature (e.g., 900° C.). With the impedance setpoint adjusted to 85Ω, the dry air pumping current of the aged oxygen sensor may be returned to the nominal dry air pumping current (e.g., 4.0 mA), as the increased dry air pumping current (e.g., 4.2 mA) may result from excessive operating temperatures reached due to utilization of the unadjusted impedance setpoint.

FIG. 5 shows a plot 500 of operating temperature as a function of impedance setpoint for an example oxygen sensor. In particular, plot 500 illustrates how, in some examples, a relatively higher impedance setpoint may be selected to achieve a desired operating temperature in an aged oxygen sensor compared to a relatively lower impedance setpoint selected to achieve the desired operating temperature in a non-aged (e.g., new) oxygen sensor. Plot 500 includes a function 502 relating the impedance setpoint to the resulting operating temperature in a non-aged oxygen sensor. In this example, 800 deg C. is the desired operating temperature, as desired oxygen sensor operation may be provided thereat. As shown in FIG. 5, an impedance setpoint of 75 ohms achieves the desired operating temperature for the non-aged oxygen sensor. In contrast, function 504 shows how the relation between impedance setpoint and resulting operating temperature is different for the aged oxygen sensor. Specifically, an impedance setpoint of 85 ohms is selected to achieve the desired operating temperature in the aged oxygen sensor. FIG. 5 generally illustrates how, in some examples, increasingly greater impedance setpoints may be selected to achieve a desired operating temperature as an oxygen sensor ages. It will be appreciated, however, that FIG. 5 is provided as an example and is not intended to be limiting. Functions 502 and 504, for example, may assume other forms (e.g., non-linear forms).

Note that the example control and estimation routines included herein can be used with various engine and/or vehicle system configurations. The control methods and routines disclosed herein may be stored as executable instructions in non-transitory memory. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method of operating an oxygen sensor, comprising:
   during a first humidity condition of gasses flowing through the oxygen sensor, determining a first pumping current of the oxygen sensor;
   during a second, different humidity condition of gasses flowing through the oxygen sensor, determining a second pumping current of the oxygen sensor;
   determining a dry air pumping current of the oxygen sensor as a function of the first and second pumping currents; and
   adjusting an impedance setpoint of the oxygen sensor based on a difference between the dry air pumping current of the oxygen sensor and a previously determined dry air pumping current.

2. The method of claim 1, further comprising adjusting a heating element coupled to the oxygen sensor responsive to the adjusted impedance setpoint.

3. The method of claim 2, wherein the impedance setpoint is adjusted based on a desired operating temperature of the oxygen sensor.

4. The method of claim 2, wherein an operating temperature of the oxygen sensor is a function of the adjusted impedance setpoint.

5. The method of claim 2, further comprising prior to adjusting the impedance setpoint, determining the dry air pumping current during selected conditions.

6. The method of claim 5, wherein the oxygen sensor is an exhaust oxygen sensor, and wherein the selected conditions include non-fueling conditions.

7. The method of claim 6, wherein the non-fueling conditions include deceleration fuel shut-off.

8. The method of claim 5, wherein the oxygen sensor is an intake oxygen sensor, and wherein the selected conditions include no purge or crankcase ventilation gasses being received in an intake manifold and exhaust gas recirculation being enabled.

9. The method of claim 2, wherein adjusting the heating element responsive to the adjusted impedance setpoint includes measuring an impedance of the oxygen sensor.

10. The method of claim 2, further comprising:
    storing the adjusted impedance setpoint in a data structure; and
    retrieving the adjusted impedance setpoint from the data structure based on a desired operating temperature of the oxygen sensor.

11. The method of claim 2, wherein the impedance setpoint is adjusted to compensate for aging of the oxygen sensor.

12. A method of operating an oxygen sensor, comprising:
determining a dry air pumping current of the oxygen sensor as a function of a first pumping current measured during application of a first positive voltage to the oxygen sensor and a second pumping current measured during application of a second, higher positive voltage to the oxygen sensor; and
compensating a change in a relation between an impedance setpoint of the oxygen sensor and a resulting operating temperature of the oxygen sensor by adjusting the impedance setpoint based on a change in the dry air pumping current of the oxygen sensor from a previously determined dry air pumping current.

13. The method of claim 12, further comprising heating the oxygen sensor to the resulting operating temperature via a heating element controlled according to the adjusted impedance setpoint.

14. The method of claim of 12, wherein the change in the dry air pumping current corresponds to a difference between the dry air pumping current and a nominal dry air pumping current of a non-aged oxygen sensor.

15. The method of claim 1, wherein determining the first pumping current comprises applying a first positive voltage to the oxygen sensor and reading an output of the oxygen sensor, and wherein determining the second pumping current comprises applying a second, higher positive voltage to the oxygen sensor and reading the output of the oxygen sensor.

16. The method of claim 1, wherein the previously determined dry air pumping current is a dry air pumping current of a non-aged oxygen sensor.

17. The method of claim 12, wherein the previously determined dry air pumping current is a dry air pumping current of a non-aged oxygen sensor.

18. The method of claim 12, wherein the first positive voltage has a value at which, during application of the first positive voltage to the oxygen sensor, oxygen is pumped from a cell of the oxygen sensor but $H_2O$ is not dissociated, and wherein the second positive voltage has a value at which, during application of the second positive voltage to the oxygen sensor, $H_2O$ in the oxygen pumped from the cell is at least partially dissociated.

* * * * *